(12) United States Patent
Hung et al.

(10) Patent No.: US 8,173,171 B2
(45) Date of Patent: May 8, 2012

(54) HYDROGEL MICROPARTICLE COMPOSITION, APPLICATION THEREOF AND METHOD FOR PREPARING THE SAME

(75) Inventors: Yu-Chun Hung, Taoyuanhsien (TW); Chi-Shu Wei, Shulin (TW); Lien-Hua Chiu, Yonghe (TW); Wen-Yen Chiu, Taipei (TW); Chia-Jen Wen, Taipei (TW)

(73) Assignee: Taiwan Textile Research Institute, Taipei Hsien (TW)

( * ) Notice: Subject to any disclaimer, the term of this patent is extended or adjusted under 35 U.S.C. 154(b) by 221 days.

(21) Appl. No.: 12/729,376

(22) Filed: Mar. 23, 2010

(65) Prior Publication Data

US 2010/0178345 A1 Jul. 15, 2010

Related U.S. Application Data

(63) Continuation-in-part of application No. 10/968,283, filed on Oct. 18, 2004, now abandoned.

(30) Foreign Application Priority Data

Nov. 17, 2003 (TW) .............................. 92132185 A

(51) Int. Cl.
 *A61K 9/14* (2006.01)
(52) U.S. Cl. ........................................................ 424/489
(58) Field of Classification Search .................. None
 See application file for complete search history.

(56) References Cited

U.S. PATENT DOCUMENTS

| 4,028,290 A | 6/1977 | Reid |
| 4,956,350 A | 9/1990 | Mosbey |
| 5,420,197 A | 5/1995 | Lorenz et al. |
| 5,834,007 A | 11/1998 | Kubota |
| 5,853,867 A | 12/1998 | Harada et al. |
| 5,977,428 A | 11/1999 | Bozigian et al. |
| 6,486,213 B1 | 11/2002 | Chen et al. |
| 6,927,268 B2 * | 8/2005 | Matsumoto et al. ....... 526/317.1 |
| 6,960,617 B2 | 11/2005 | Omidian et al. |
| 2002/0143081 A1 * | 10/2002 | Li et al. .................. 523/201 |

FOREIGN PATENT DOCUMENTS

TW 394689 12/1986

OTHER PUBLICATIONS

Lee et al "Morphology and Temperature Responsiveness-swlling Relationship of Poly(N-isopropylamide-chitosan) Copolymers and Their Application to Drug Release", Journal of Polymer Science: Part A:Polymer Chemistry, vol. 42, May 13, 2004, pp. 3029-3037.*
Bae et al "Thermosensitive Chitosan as an Injectable Carrier for Local Drug Delivery" Macromolecular Research, vol. 14, p. 461-465 (2006).*
Leung et al "New Route to Smart Core-Shell Polymeric Microgels: Synthesis and Properties" Marcomol. Rapid Commun., 2004, 25, 1819-1823.*
Lie et al "Preparation of Poly(N-isopropylacrylamide-g-chitosan) Microparticles and Their Controlled Drug Release Property", Chinese Journal of Synthetic Chemistry (May 2008), vol. 16, No. 5, p. 516-518.*

* cited by examiner

*Primary Examiner* — Bethany Barham
(74) *Attorney, Agent, or Firm* — Thomas, Kayden, Horstemeyer & Risley, LLP

(57) ABSTRACT

Disclosed herein is a method for preparing a hydrogel microparticle composition. A dispersion including 1 part by weight of N-isopropyl acrylamide, about 0.1-0.5 part by weight of chitosan, about 0-0.05 part by weight of N,N'-methylene bisacrylamide, about 0.1-0.5 part by weight of glacial acetic acid, and about 20-40 parts by weight of water is prepared. About 0.01-0.3 part by weight of an anionic initiator is added into the dispersion and the dispersion is allowed to undergo a polymerization reaction at a temperature of about 10-100° C. for about 1 to 5 hours, thereby producing a plurality of hydrogel microparticles dispersed in the water to form the hydrogel microparticle composition.

15 Claims, No Drawings

HYDROGEL MICROPARTICLE COMPOSITION, APPLICATION THEREOF AND METHOD FOR PREPARING THE SAME

CROSS-REFERENCE

The present application is a continuation-in-part application of U.S. application Ser. No. 10/968,283, filed Oct. 18, 2004, and claims priority to Taiwanese Application Serial Number 92132185, filed Nov. 17, 2003. The entire disclosures of all the above applications are hereby incorporated by reference herein.

BACKGROUND

1. Field of Invention

The present invention relates to a hydrogel microparticle composition. More particularly, the present invention relates to a composite hydrogel microparticle composition containing chitosan.

2. Description of Related Art

Hydrogels have been applied widely in biomedical fields, such as wound dressings, haemostatic materials, controlled drug release system and so on. Moreover, hydrogel can be used as artificial intraocular lens and implants for plastic surgery. In the recent development, composite hydrogels with additional function(s) have been given more and more attention. Such composite hydrogels can be applied in the fields of artificial skins, wound dressings, cell and tissue cultures, face masks and the like.

In U.S. Pat. No. 6,486,213, Chen et al. disclose block and graft copolymers, and hydrogels thereof, which contain both a temperature-sensitive polymer component and a pH-sensitive polymer component. Such copolymers can be used for topical drug delivery to a treatment area. According to the method and example described in Chen et al., the resulting grafted copolymer is a disk-like or sheet-like hydrogel.

Kubota, in U.S. Pat. No. 5,834,007, discloses a polymer, which has a sol-gel transition temperature in an aqueous solution. The polymer has a substantial water-insolubility at a temperature higher than the sol-gel transition temperature, thereby existing in a gel-state. The polymer has a reversible water-solubility at a temperature lower than the sol-gel transition temperature, thereby existing in a sol-state.

In U.S. Pat. No. 5,420,197, Lorenz et al. disclose a dermatologically-compatible composition comprising a hydrophilic gel which comprises a blend of a neutralized chitosan and a hydrophilic poly (N-vinyl lactam). The product is used in, for example, wound dressings, burn dressings, drug delivery dressings, cosmetic mask dressings, and the like.

A highly absorbent modified polysaccharide is taught by Reid et al. in U.S. Pat. No. 4,028,290. According to Reid et al., the modified polysaccharides are prepared by reacting a polysaccharide such as cellulose or starch in the presence of acrylamide, another vinyl monomer and a divinyl crosslinking monomer using free radical polymerization techniques. The product is a complex mixture of crosslinked grafted polysaccharide and acrylamide copolymers. Reid et al. also teach that product is water soluble, and hence, it is desirable to keep the amount of the water relatively low with respect to the reactants so that a relatively high vinyl monomer concentration will be maintained in the vicinities of the polysaccharide particles. To this end, only enough water is used to dissolve the monomers and uniformly wet the polysaccharide, about 1.5 to 2.5 parts per part of reactants. Moreover, according to Reid et al., an inert water-immiscible diluent, such as toluene, is employed as the reaction medium; otherwise, the yields of the products are substantially lowered.

Omidian et al., in U.S. Pat. No. 6,960,617, disclose porous or superporous hydrogels having improved elasticity and mechanical strength properties. The porous or superporous hydrogels are obtained by subjecting a hydrogel formulation containing a strengthening agent to chemical or physical crosslinking conditions subsequent to initial gel formation. According to Omidian et al., it is important to control the monomer concentration (dilution with water) and comonomer (acrylic acid) concentration so as to achieve a desirable gelation property that results in the porous or superporous hydrogels.

The above-identified documents teach hydrogels in the form of bulk materials, and neither of them discloses hydrogel particles and methods for preparing the same.

Bozigian et al., on the other hand, disclose a method for preparing hydrogel particles in U.S. Pat. No. 5,977,428. According to Bozigian et al., polyacrylonitrile (PAN) is formed as a solid aquagel, and the PAN aquagel is subjected to a base hydrolysis and then dried to obtain the hydrogel particles.

Conventionally, the hydrogel particles are prepared in a two-stage manner, such as the method described in Bozigian et al. Specifically, the bulk hydrogel material is first formed in the formed of a block polymer (or copolymer, grafted polymer), and then the hydrogel is processed (dried or granulized) to produce hydrogel particles.

In view of the forgoing, there exists a need in the related art to provide a method for preparing hydrogel microparticles of substantially uniform particle sizes.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present invention is directed to a method for preparing a hydrogel microparticle composition. According to the method disclosed herein, the hydrogel microparticles can be prepared during the polymerization process, which is less complicated than the conventional methods. In addition, the hydrogel microparticles thus-prepared are composite hydrogel microparticles containing chitosan. Moreover, the hydrogel microparticles thus-prepared have substantially uniform particle sizes.

According to one embodiment of the present invention, the method includes the steps as follows. A dispersion including 1 part by weight of N-isopropyl acrylamide, about 0.1-0.5 part by weight of chitosan, about 0-0.05 part by weight of N,N'-methylene bisacrylamide, about 0.1-0.5 part by weight of glacial acetic acid, and about 20-40 parts by weight of water is prepared. About 0.01-0.3 part by weight of an anionic initiator is added into the dispersion and the dispersion is allowed to undergo a polymerization reaction at a temperature of about 10-100° C. for about 1 to 5 hours, thereby producing a plurality of hydrogel microparticles dispersed in the water to form the hydrogel microparticle composition.

In another aspect, the present invention is directed to a hydrogel microparticle composition. The hydrogel microparticle composition is prepared by the method according to the first aspect of the present invention.

According to one embodiment of the present invention, the hydrogel microparticle composition includes a plurality of hydrogel microparticles including a copolymer formed by reacting 1 part by weight of N-isopropyl acrylamide, about 0.1-0.5 part by weight of chitosan with about 0-0.05 part by weight of N,N'-methylene bisacrylamide under the action of about 0.01-0.3 part by weight of an anionic initiator and about 0.1-0.5 part by weight of glacial acetic acid, and about 20-40 parts by weight of water, wherein the plurality of hydrogel microparticles have an average diameter of 70-380 μm and are dispersed in the water.

In yet another aspect, the present invention is directed to a biomedical material. The biomedical material employs the hydrogel microparticle composition provided herein and exhibits efficacy in absorbing and releasing the active agent (s) in a controlled way.

According to one embodiment of the present invention, the biomedical material comprises a hydrogel microparticle composition of the previous aspect of the present invention; and a water-soluble active agent absorbed in the plurality of hydrogel microparticles.

Many of the attendant features will be more readily appreciated as the same becomes better understood by reference to the following detailed description considered in connection with the accompanying drawings.

DETAILED DESCRIPTION

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Environment-sensitive hydrogels have the potential to be used in a drug delivery system. Generally, environment-sensitive hydrogels are sensitive to physical and/or chemical stimulations. Examples of environment-sensitive hydrogels include but are not limited to: light-sensitive hydrogels, electric field-sensitive hydrogels, temperature-sensitive hydrogels, pH-sensitive hydrogels, solvent-sensitive hydrogels and ionic strength-sensitive hydrogels. For example, the temperature-sensitive and pH-sensitive hydrogels are capable of absorbing active agent(s) in a specific temperature or pH condition then releasing the same in the physiological temperature or pH of a human subject.

Hydrogels may be presented in the form of bulk hydrogel and hydrogel particles. Hydrogel particles have greater specific surface area than the bulk hydrogel of the same weight. As such, hydrogel particles may absorb more active agent(s) than the bulk hydrogel. Moreover, hydrogel particles of smaller particle sizes may absorb more active agent(s) than hydrogel particles of greater particle sizes of the same weight. Accordingly, it is more preferable to use hydrogel particles of smaller particle sizes As stated in the Description of Related Art, conventional methods for preparing hydrogel particles involve forming a bulk hydrogels first, and then drying or granulizing the bulk hydrogels to obtain hydrogel particles. The two-stage preparation method is time-consuming and cost-ineffective. Moreover, the hydrogel particles thus obtained usually have larger diameters; and hence, in some cases, the dried hydrogel particles should be further grinded into particles of smaller sizes. For example, Bozigian et al. disclose hydrogel particles, after being grinded, having sizes of 0.5 to 200 mm.

In view of the foregoing, a method for preparing a hydrogel microparticle composition is provided by the present invention. According to the method disclosed herein, the hydrogel microparticles can be prepared in a single polymerization step. Hence, the method is less complicated than the conventional methods. Moreover, the hydrogel microparticles thus-prepared have particle sizes on a micrometer scale. In addition, the hydrogel microparticles thus-prepared are composite hydrogel microparticles containing chitosan.

According to one embodiment of the present invention, the method includes the steps as follows. A dispersion including 1 part by weight of N-isopropyl acrylamide (NIPAAm), about 0.1-0.5 part by weight of chitosan, about 0-0.05 part by weight of N,N'-methylene bisacrylamide (MBA), about 0.1-0.5 part by weight of glacial acetic acid (GAA), and about 20-40 parts by weight of water is prepared. About 0.01-0.3 part by weight of an anionic initiator is added into the dispersion and the dispersion is allowed to undergo a polymerization reaction at a temperature of about 10-100° C. for about 1 to 5 hours, thereby producing a plurality of hydrogel microparticles dispersed in the water to form the hydrogel microparticle composition.

According to the above-described method, the NIPAA and the chitosan are co-polymerized under the initiation of APS, and the MBA is used to crosslink the copolymer. During the polymerization, the surfaces of the chitosan molecules are positively charged due to the presence of the glacial acetic acid. The positive charges of the chitosan would act as a surfactant in the reaction system containing an anionic initiator. As such, by using the positively charged to chitosan and the anionic initiator, it is possible to prevent the reaction system from coagulation. Therefore, hydrogel microparticles, rather than a bulk hydrogel, are produced during the polymerization.

Examples of the anionic initiator include, but are not limited to, ammonium persulfate (APS), sodium methoxide, sodium ethoxide, potassium butoxide, and potassium tert-butoxide. In the working examples presented hereinbelow, APS was used as the initiator.

According to various embodiments of the present invention, the amount of chitosan is about 0.1, 0.2, 0.3, 0.4, or 0.5 part by weight based on 1 part by weight of NIPAAm. Preferably, the weight ratio of chitosan to NIPAAm is about 0.3 to 0.5.

According to various embodiments of the present invention, the amount of MBA is about 0, 0.01, 0.02, 0.03, 0.04, or 0.05 part by weight based on 1 part by weight of NIPAAm. Preferably, the weight ratio of MBA to NIPAAm is about 0.03 to 0.04.

According to various embodiments of the present invention, the amount of glacial acetic acid is about 0.1, 0.2, 0.3, 0.4, or 0.5 part by weight based on 1 part by weight of NIPAAm. Preferably, the weight ratio of glacial acetic acid to NIPAAm is about 0.02 to 0.03.

According to various embodiments of the present invention, the amount of water is about 20, 21, 22, 23, 24, 25, 26, 27, 28, 29, 30, 31, 32, 33, 34, 35, 36, 37, 38, 39 or 40 part by weight based on 1 part by weight of NIPAAm. Preferably, the weight ratio of water to NIPAAm is about 30-40.

According to various embodiments of the present invention, the amount of the anionic initiator (for example, APS) is about 0.01, 0.05, 0.1, 0.15, 0.2, 0.25 or 0.3 part by weight based on 1 part by weight of NIPAAm. Preferably, the weight ratio of chitosan to NIPAAm is about 0.1-0.2.

Since the main constituents in the reaction system is water, the polymerization reaction can be carried out in the operable temperature range of the water (that is, about 0° C. to about 100° C.). Preferably, the polymerization reaction could be carried out at a reaction temperature of about 10-100° C. More preferably, the reaction temperature can be about 20-90° C., 30-80° C., 40-70° C., or 50-60° C.

The reaction time for the polymerization is about 1 to 5 hours; preferably about 2 to 4 hours; and more preferably, about 3-3.5 hours.

According to the working examples of the present invention, the hydrogel microparticle thus-obtained comprises a plurality hydrogel microparticles having an average diameter of 70-380 μm. For example, the average diameter of the hydrogel microparticles can be about 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, and 380 μm.

Also, the hydrogel microparticle thus-obtained is a temperature sensitive hydrogel having a lower critical solution temperature (LCST) of about 30-37° C.; preferably, about 34-36° C. For example, the LCST may be about 30, 30.5, 31, 31.5, 32, 32.5, 33, 33.5, 34, 34.5, 35, 35.5, 36, 36.5, or 37° C.

According to embodiments of the present invention, the hydrogel microparticle composition can be dried to obtain a powder or a film of the hydrogel microparticle composition. For example, a spray drying or vacuum drying process can be carried out so that the hydrogel microparticles are dried into powder. Alternatively, the hydrogel microparticle composition may be sprayed or coated as a thin layer, and then the liquid of the composition is removed whereby forming a film of the hydrogel microparticle.

Alternatively, the hydrogel microparticle composition can be mixed with solvent(s) so as to obtain a liquid, latex or gel containing the hydrogel microparticle composition.

Also disclosed herein is a hydrogel microparticle composition. Generally, the hydrogel microparticle composition is prepared in accordance with the above-mentioned aspect/embodiments of the present invention.

According to embodiments of the present invention, the hydrogel microparticle composition includes a plurality of hydrogel microparticles including a copolymer formed by reacting 1 part by weight of N-isopropyl acrylamide, about 0.1-0.5 part by weight of chitosan with about 0-0.05 part by weight of N,N'-methylene bisacrylamide under the action of about 0.01-0.3 part by weight of ammonium persulfate and about 0.1-0.5 part by weight of glacial acetic acid; and about 20-40 parts by weight of water, wherein the plurality of hydrogel microparticles have an average diameter of 70-380 μm and are dispersed in the water.

Some working examples according to embodiments of the present disclosure and comparative examples are provided hereinafter. In those examples, various compositions were employed to prepared hydrogels, and the hydrogels thus-obtained were tested for some properties thereof. In addition, caffeine calibration test was performed to quantitatively measure the weight percent of caffeine retained within the hydrogel.

Experiment 1

In experiment 1, various hydrogels were prepared by using the compositions summarized in Table 1. The weights of the constituents are presented as part by weight (PBW). For example, in working example 1, 7 grams (1 PBW) of NIPAAm, 0.21 grams (0.03 PBW) of MBA, 0.7 grams (0.1 PBW) of chitosan, 280 grams (40 PBWs) of deionized water and 3 grams (0.43 PBW) of glacial acetic acid were mixed in a 2 L-reaction flask to form a reaction system. The reaction system was stirred at room temperature with a stirrer until the reaction system was substantially homogeneous. After that, the reaction system was heated to and maintained at about 50° C. Meanwhile, the reaction system was rotated at a speed of 300 rpm and 0.7 grams (0.1 PBW) of APS was added into the reaction system. The reaction system was allowed for polymerization for about 3 hours. The product thus obtained is a hydrogel microparticle composition including a plurality of hydrogel microparticles dispersed therein. Comparative examples were prepared in the similar way without the addition of the chitosan.

For measuring the average swelling diameter ("Diameter" as presented in Table 1 and the following tables) of the hydrogel microparticles present in the hydrogel microparticle composition, the composition was diluted with water such that the dilution contained about 9% by weight of hydrogel microparticles therein; and then the diameter was measured by a light scattering particle size analyzer.

The zeta potential ("Potantial" as presented in Table 1 and the following tables) of the hydrogel microparticle composition was determined by a zeta meter.

LCST of the composition is determined based on relationship between the swelling ratio and the temperature. To measure the swelling ratio (SR) of the hydrogel microparticle composition, the composition was cast in a Teflon casting plate. The casted composition together with the casting plate was dried in an oven at 50° C. for one day (24 hours) to obtain a chip. The chip was weighted (Wd) before being immersed in the deionized water of a specific temperature. The chip was wiped and again weighted (Ws) after being immersed for 1 hour. The swelling ratio of the chip at the specific temperature was determined as follows:

$$SR\% = (Ws - Wd)/Wd * 100\%$$

The average swelling diameter, zeta potential and LCST of the hydrogel microparticle composition are also presented in Table 1.

TABLE 1

| | Chitosan (PBW) | NIPAAm (PBW) | MBA (PBW) | Water (PBW) | APS (PBW) | GAA (PBW) | Diameter (μm) | Potantial (mV) | LCST (° C.) |
|---|---|---|---|---|---|---|---|---|---|
| | | | | Working Example | | | | | |
| 1 | 0.1 | 1 | 0.03 | 40 | 0.1 | 0.43 | 375.25 | −2.20 | 33 |
| 2 | 0.2 | 1 | 0.03 | 40 | 0.1 | 0.43 | 162.92 | −1.85 | 32.5 |
| 3 | 0.3 | 1 | 0.03 | 40 | 0.1 | 0.43 | 75.30 | 5.97 | 32 |
| 4 | 0.5 | 1 | 0.03 | 40 | 0.1 | 0.43 | — | 6.87 | 34 |
| 5 | 0.1 | 1 | 0.05 | 40 | 0.1 | 0.43 | 125.17 | −2.40 | — |
| 6 | 0.2 | 1 | 0.05 | 40 | 0.1 | 0.43 | — | −1.05 | 34 |
| 7 | 0.3 | 1 | 0.05 | 40 | 0.1 | 0.43 | 75.25 | 6.50 | — |
| 8 | 0.5 | 1 | 0.05 | 40 | 0.1 | 0.43 | — | 3.73 | — |
| 9 | 0.1 | 1 | 0 | 40 | 0.1 | 0.43 | — | −1.60 | — |

TABLE 1-continued

| | Chitosan (PBW) | NIPAAm (PBW) | MBA (PBW) | Water (PBW) | APS (PBW) | GAA (PBW) | Diameter (μm) | Potantial (mV) | LCST (° C.) |
|---|---|---|---|---|---|---|---|---|---|
| 10 | 0.2 | 1 | 0 | 40 | 0.1 | 0.43 | — | −16.5 | — |
| 11 | 0.3 | 1 | 0 | 40 | 0.1 | 0.43 | — | 0.65 | — |
| 12 | 0.5 | 1 | 0 | 40 | 0.1 | 0.43 | — | −1.15 | — |
| 13 | 0.2 | 1 | 0.03 | 40 | 0.1 | 0.14 | — | 2.89 | — |
| 14 | 0.2 | 1 | 0.03 | 40 | 0.029 | 0.43 | — | 3.92 | — |
| 15 | 0.2 | 1 | 0.03 | 40 | 0.1 | 0.43 | — | 2.20 | — |
| 16 | 0.2 | 1 | 0.03 | 40 | 0.2 | 0.43 | — | −1.45 | — |
| 17 | 0.2 | 1 | 0.03 | 40 | 0.3 | 0.43 | — | −2.40 | — |
| 18 | 0.2 | 1 | 0.01 | 40 | 0.1 | 0.43 | — | — | 30 |
| 19 | 0.2 | 1 | 0.1 | 40 | 0.1 | 0.43 | — | — | 33.5 |
| Comparative Example | | | | | | | | | |
| 1 | 0 | 1 | 0 | 40 | 0.1 | | — | −2.85 | — |
| 2 | 0 | 1 | 0.03 | 40 | 0.1 | | — | −3.35 | — |
| 3 | 0 | 1 | 0.05 | 40 | 0.1 | | — | −2.90 | — |

By comparing working examples 1 to 3, it is found that the chitosan/NIPAAm ratio may affect the particle size of the hydrogel microparticles. More specifically, the average diameter of the swelled hydrogel microparticle may decrease with the increasing chitosan/NIPAAm ratio. Similar results can be observed in working examples 4 and 6. Without being bound to any theory, it is believed that the chitosan may provide a surfactant effect during the polymerization process thereby resulting hydrogel microparticles with smaller diameters.

Results of comparative example 1 and working examples 1-4 and 5-8 show that the chitosan concentration is positively related to the zeta potential of the hydrogel microparticle composition. Generally, a lower zeta potential suggests a smaller average particle diameter, and thus is preferred in accordance to the principle and the spirit of the present invention. In addition, a lower surface potential may also increase the stability of the hydrogel microparticle composition whereby preventing the microparticles from coagulation.

The comparison between the working examples 1 and 5 suggests that the concentration of the crosslinking agent (MBA) may also affect the diameter of the hydrogel microparticle. Higher concentration of the crosslinking agent would result in higher degree of nucleation which may in turn reduce the particle size.

In working examples 2 and 13, it is shown that the concentration of the glacial acetic acid is negatively related to the zeta potential. That is, the zeta potential of the hydrogel composition decrease as the concentration of the glacial acetic acid increases.

Results of working examples 14-17 suggest that the amount of the initiator (APS) is also negatively related to the zeta potential.

LCST analysis was carried out to investigate the LCST of hydrogel compositions according to some, but not all, working examples, and the results are summarized in Table 1 hereinabove. For example, the hydrogel compositions of examples 4 and 6 each has an LCST of about 34° C.

In view of the foregoing, the methods for preparing a hydrogel microparticle composition according to the present invention have at least the advantages as follows.

For a start, hydrogel microparticle composition having a plurality of hydrogel microparticles can be prepared in a single step using dispersion polymerization.

Further, the polysaccharide or derivatives thereof such as chitosan may provide a surfactant effect during the dispersion polymerization; hence eliminating the need to use a detergent and/or an emulsifier that should not present in the final product.

Moreover, the chitosan may endow the hydrogel microparticle composition with additional functionality such as antimicrobial, deodorization, hemostasis, and so on.

Last but not least, the present invention teaches that the properties, such as zeta potential and particle size, of the hydrogel microparticle composition may be adjusted by altering the proportions of the constituents for preparing the hydrogel microparticle composition.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for preparing a hydrogel microparticle composition, comprising:
    preparing a dispersion comprising 1 part by weight of N-isopropyl acrylamide, about 0.1-0.5 part by weight of chitosan, about 0.03-0.05 part by weight of N,N'-methylene bisacrylamide, about 0.1-0.5 part by weight of glacial acetic acid, and about 20-40 parts by weight of water;
    adding about 0.01-0.3 part by weight of an anionic initiator into the dispersion and allowing the dispersion to undergo a polymerization reaction at a temperature of about 10-100° C. for about 1 to 5 hours, thereby producing a plurality of hydrogel microparticles dispersed in the water to form the hydrogel microparticle composition.

2. The method of claim 1, wherein the hydrogel microparticles has an average diameter of 70-380 μm.

3. The method of claim 1, wherein the hydrogel microparticle composition has a lower critical solution temperature of about 30-37° C.

4. The method of claim 1, further comprising adding the hydrogel microparticle composition into a solvent to obtain a liquid, latex or gel containing the hydrogel microparticle composition.

5. The method of claim 1, further comprising drying the hydrogel microparticle composition to obtain a powder or a film of the hydrogel microparticle.

6. The method of claim 1, wherein the anionic initiator is ammonium persulfate, sodium methoxide, sodium ethoxide, potassium butoxide, or potassium tert-butoxide.

7. A hydrogel microparticle composition, comprising:
   a plurality of hydrogel microparticles comprising a copolymer formed by reacting about 1 part by weight of N-isopropyl acrylamide, about 0.1-0.5 part by weight of chitosan with about 0.03-0.05 part by weight of N,N'-methylene bisacrylamide under the action of about 0.01-0.3 part by weight of an anionic initiator and about 0.1-0.5 part by weight of glacial acetic acid; and
   about 20-40 parts by weight of water, wherein the plurality of hydrogel microparticles have an average diameter of 70-380 μm and are dispersed in the water.

8. The hydrogel microparticle composition of claim 7, wherein the hydrogel microparticle composition has a lower critical solution temperature of about 30-37° C.

9. The hydrogel microparticle composition of claim 7, wherein the anionic initiator is ammonium persulfate, sodium methoxide, sodium ethoxide, potassium butoxide, or potassium tert-butoxide.

10. The hydrogel microparticle composition of claim 7, wherein the hydrogel microparticle composition is suspended in a solvent to obtain a liquid, latex or gel containing the hydrogel microparticle composition.

11. The hydrogel microparticle composition of claim 7, wherein the hydrogel microparticle composition is dried to obtain a powder of a film of the hydrogel microparticle.

12. A biomedical material, comprising:
    a hydrogel microparticle composition of claim 7; and
    a water-soluble active agent absorbed in the plurality of hydrogel microparticles.

13. The biomedical material of claim 12, wherein the hydrogel microparticle composition has a lower critical solution temperature of about 30-37° C.

14. The biomedical material of claim 12, wherein the water-soluble active agent is absorbed in the plurality of hydrogel microparticles at a temperature no greater than the lower critical solution temperature of the hydrogel microparticle composition and is released from the plurality of hydrogel microparticles at a temperature greater than the lower critical solution temperature of the hydrogel microparticle composition.

15. The biomedical material of claim 12, wherein the biomedical material is used as a wound dressing, a haemostatic material, or a drug delivery system.

* * * * *